(12) United States Patent
Brazdil et al.

(10) Patent No.: US 7,727,928 B2
(45) Date of Patent: Jun. 1, 2010

(54) CATALYST COMPOSITION AND USE THEREOF IN ETHANE OXIDATION

(75) Inventors: James Frank Brazdil, Glen Ellyn, IL (US); Richard J George, Oswego, IL (US); Bruce I Rosen, Park Ridge, IL (US)

(73) Assignee: BP Chemicals Limited, Middlesex (GB)

( * ) Notice: Subject to any disclaimer, the term of this patent is extended or adjusted under 35 U.S.C. 154(b) by 0 days.

(21) Appl. No.: 12/461,050

(22) Filed: Jul. 30, 2009

(65) Prior Publication Data

US 2009/0292139 A1    Nov. 26, 2009

Related U.S. Application Data

(62) Division of application No. 10/568,767, filed as application No. PCT/GB2004/003302 on Jul. 30, 2004, now abandoned.

(51) Int. Cl.
| | |
|---|---|
| *B01J 23/20* | (2006.01) |
| *C07C 27/14* | (2006.01) |
| *C07C 51/215* | (2006.01) |
| *C07C 51/25* | (2006.01) |
| *B01J 23/24* | (2006.01) |
| *B01J 23/14* | (2006.01) |

(52) U.S. Cl. .............. 502/308; 562/512.2; 502/311; 502/310; 502/312

(58) Field of Classification Search ............ 502/308, 502/310, 311, 312; 562/512.2
See application file for complete search history.

(56) References Cited

U.S. PATENT DOCUMENTS

| | | | |
|---|---|---|---|
| 4,250,346 A | 2/1981 | Young et al. | ............ 585/658 |
| 2002/0099239 A1* | 7/2002 | Ellis et al. | ............ 560/241.1 |
| 2003/0088118 A1 | 5/2003 | Komada et al. | |

FOREIGN PATENT DOCUMENTS

| | | |
|---|---|---|
| EP | 0 294 846 A2 | 12/1988 |
| WO | WO 99/51339 | 10/1999 |
| WO | WO 03/033138 A1 | 4/2003 |

* cited by examiner

*Primary Examiner*—Timothy C Vanoy
*Assistant Examiner*—Daniel Berns
(74) *Attorney, Agent, or Firm*—Nixon & Vanderhye, PC

(57) ABSTRACT

A catalyst composition and its use for the oxidation of ethane to ethylene and acetic acid which comprises (i) a support, and (ii) in combination with oxygen, the elements molybdenum, vanadium and niobium, optionally tungsten and a component Z, which is one or more metals of Group 14 of the Periodic Table of Elements; a, b, c, d and e represent the gram atom ratios of the elements Mo, W, Z, V and Nb respectively, such that $0<a\leq1$; $0\leq b<1$ and $a+b=1$; $0.05<c\leq2$; $0<d\leq2$; and $0<e\leq1$.

28 Claims, No Drawings

CATALYST COMPOSITION AND USE THEREOF IN ETHANE OXIDATION

This application is a divisional of application Ser. No. 10/568,767, filed Feb. 21, 2006 now abandoned, which is a 371 of PCT/GB2004/003302, filed Jul. 30, 2004, the entire content of which is hereby incorporated by reference in this application.

The present invention relates to a catalyst composition for the oxidation of ethane, and optionally ethylene, to acetic acid and ethylene, and to a process for the production of acetic acid and ethylene utilizing the aforesaid catalyst composition.

Catalyst compositions comprising molybdenum, vanadium and niobium in combination with oxygen for use in processes for the production of acetic acid by the oxidation of ethane and/or ethylene are known in the art from, for example, U.S. Pat. No. 4,250,346, EP-A-1043064, WO 99/20592 and DE 196 30 832.

U.S. Pat. No. 4,250,346 discloses the oxidative dehydrogenation of ethane to ethylene and acetic acid in a gas phase reaction, at a temperature of less than about 550° C. using as a catalyst a composition comprising the elements molybdenum, X and Y in the ratio $Mo_a X_b Y_c$ wherein X is Cr, Mn, Nb, Ta, Ti, V and/or W, and preferably Mn, Nb, V and/or W; Y is Bi, Ce, Co, Cu, Fe, K, Mg, Ni, P, Pb, Sb, Si, Sn, Tl and/or U, and preferably Sb, Ce and/or U, a is 1, b is 0.05 to 1.0 and c is 0 to 2, and preferably 0.05 to 1.0, with the proviso that the total value of c for Co, Ni and/or Fe is less than 0.5.

WO 99/20592 relates to a method of selectively producing acetic acid from ethane, ethylene or mixtures thereof and oxygen at high temperature in the presence of a catalyst composition having the formula $Mo_a Pd_b X_c Y_d$ wherein X represents one or several of Cr, Mn, Nb, Ta, Ti, V, Te and W; Y represents one or several of B, Al, Ga, In, Pt, Zn, Cd, Bi, Ce, Co, Rh, Ir, Cu, Ag, Au, Fe, Ru, Os, K, Rb, Cs, Mg, Ca, Sr, Ba, Nb, Zr, Hf, Ni, P, Pb, Sb, Si, Sn, Tl and U and a=1, b=0.0001 to 0.01, c=0.4 to 1 and d=0.005 to 1.

German patent application DE 196 30 832 A1 relates to a similar catalyst composition in which a=1, b>0, c>0 and d=0 to 2. Preferably, a=1, b=0.0001 to 0.5, c=0.1 to 1.0 and d=0 to 1.0.

The catalyst compositions of both WO 99/20592 and DE 19630832 require the presence of palladium.

EP-A-1043064 discloses a catalyst composition for the oxidation of ethane to ethylene and/or acetic acid and/or for the oxidation of ethylene to acetic acid which comprises in combination with oxygen the elements molybdenum, vanadium, niobium and gold in the absence of palladium according to the empirical formula:

$$Mo_a W_b Au_c V_d Nb_e Y_f \quad (I)$$

wherein Y is one or more elements selected from the group consisting of: Cr, Mn, Ta, Ti, B, Al, Ga, In, Pt, Zn, Cd, Bi, Ce, Co, Rh, Ir, Cu, Ag, Fe, Ru, Os, K, Rb, Cs, Mg, Ca, Sr, Ba, Zr, Hf, Ni, P, Pb, Sb, Si, Sn, Tl, U, Re, Te and La; a, b, c, d, e and f represent the gram atom ratios of the elements such that: $0<a\leq 1$; $0\leq b<1$ and $a+b=1$; $10^{-5}<c\leq 0.02$; $0<d\leq 2$; $0<e\leq 1$; and $0\leq f\leq 2$.

WO 03/033138 discloses a catalyst composition for the selective oxidation of ethane to acetic acid and/or for the selective oxidation of ethylene to acetic acid which composition comprises in combination with oxygen the elements molybdenum, vanadium, niobium and gold in the absence of palladium according to the empirical formula:

$$Mo_a W_b Au_c V_d Nb_e Z_f \quad (I)$$

wherein Z is one or more elements selected from the group consisting of: B, Al, Ga, In, Ge, Sn, Pb, Sb, Cu, Pt, Ag, Fe and Re; a, b, c, d, e and f represent the gram atom ratios of the elements such that: $0<a\leq 1$; $0\leq b<1$ and $a+b=1$; $10^{-5}<c\leq 0.02$; $0<d\leq 2$; $0<e\leq 1$; and $0.0001\leq f\leq 0.05$. Preferably, Z is Sn. Said catalysts give high selectivity to acetic acid in combination with low, if any, selectivity to ethylene.

Acetic acid may be reacted with ethylene, in the presence of oxygen, to produce vinyl acetate. In particular, it is desirable to provide an integrated process for vinyl acetate production comprising a first step for the production of acetic acid and ethylene from ethane, and optionally ethylene, followed by subsequent reaction of said acetic acid and ethylene to produce vinyl acetate. Ideally the molar ratio of ethylene to acetic acid produced in the first step is approximately 1:1.

WO 01/90042 and WO 01/90043 both disclose an integrated process for the production of vinyl acetate, the first step of which is the oxidation of ethane to acetic acid and ethylene, with subsequent conversion of the acetic acid and ethylene to vinyl acetate.

EP-A-0 877 727 discloses an integrated process for the production of acetic acid and/or vinyl acetate in any predetermined and variable proportions from a gaseous feedstock comprising ethylene and/or ethane. The integrated process comprises a first step wherein ethylene and/or ethane is catalytically oxidized in a first reaction zone to produce a first product stream comprising acetic acid, water and ethylene and optionally ethane, carbon monoxide and/or carbon dioxide. The acetic acid and ethylene produced in this first reaction zone are then contacted in a second reaction zone with a molecular oxygen-containing gas in the presence of a catalyst to produce a second product stream comprising vinyl acetate, water, acetic acid and optionally ethylene.

There remains a need to develop a catalyst composition for the oxidation of ethane, and optionally ethylene, to acetic acid and ethylene with high overall selectivity to acetic acid and ethylene and a reduced molar ratio of ethylene to acetic acid.

Surprisingly, it has now been found that by using a catalyst composition comprising molybdenum, vanadium, niobium in combination with oxygen, supported on a suitable support, and wherein said catalyst composition further comprises a component Z, which is one or more metals of Group 14 of the Periodic Table of the Elements, i.e. Ge, Sn and Pb, ethane, and optionally ethylene, may be oxidized to acetic acid and ethylene with high overall selectivity to acetic acid and ethylene.

Advantageously, it has been found that by using the catalyst composition of the present invention the ratio of acetic acid and ethylene produced may be approximately 1:1, the preferred ratio for subsequent reaction with oxygen to produce vinyl acetate. Furthermore, high overall selectivity may be achieved in the substantial absence of noble metals such as gold and/or palladium in the catalyst composition.

Accordingly, in a first aspect, the present invention provides a catalyst composition for the oxidation of ethane, and optionally ethylene, to acetic acid and ethylene, which catalyst composition comprises (i) a support, and (ii), in combination with oxygen, the elements molybdenum, vanadium and niobium, optionally tungsten and a component Z, which is one or more metals of Group 14 of the Periodic Table of Elements; wherein a, b, c, d and e represent the gram atom ratios of the elements Mo, W, Z, V and Nb respectively, such that:

$0<a\leq 1$; $0\leq b<1$ and $a+b=1$;

$0.05<c\leq 2$;

$0<d\leq 2$; and $0<e\leq 1$.

Preferably a>0.01, such as a=1. Preferably c≧0.1. Preferably, d≧0.1, such as 0.1≦d≦0.5. Preferably, e>0.01. Preferably, e≦0.6, such as 0.01≦e≦0.6.

The catalyst compositions according to the present invention may optionally comprise a further component, Y, which is one or more elements selected from the group consisting of: Cr, Mn, Ta, B, Al, Ga, In, Pt, Zn, Cd, Bi, Ce, Co, Rh, Ir, Cu, Ag, Fe, Ru, Os, K, Rb, Cs, Mg, Ca, Sr, Ba, Ni, P, Sb, Si, Tl, U, Re, Te, La, Ti, Zr, Hf, Au and Pd.

Y may be present at a gram atom ratio, f, wherein 0≦f≦2. Preferably, f≧0.01. Preferably, f≦0.5, such as 0.01≦f≦0.5.

More preferably, the catalyst compositions according to the present invention are substantially devoid of noble metals, such as gold and palladium.

Most preferably, Y, when present, is selected from the group consisting of Bi, Ca, Ce, Cu, K, P, Sb, La, Ti, Zr, Hf and Te and is most preferably selected from Ti and Zr.

The catalyst composition of the present invention comprises a support. The support may be a non-oxide support, such as silicon carbide or graphite, but is preferably selected from one or more metal oxide supports, such as silica, titania, titanosilicates, alumina, aluminosilicates, zirconia or combinations thereof, such as a mixture of silica and titania. Preferred supports include silica, titania and mixtures of titania and silica supports.

Certain elements, such as aluminium, titanium and zirconium, may be present in the catalyst composition of the present invention as a component of the support and/or as component Y.

The catalyst composition of the present invention comprises a component, Z, which is one or more of Ge, Sn and Pb. Preferably Z is Sn. Advantageously, it has been found that the addition of component Z at the gram atom ratios according to the present invention, alters the ratio of ethylene to acetic acid produced compared to an equivalent catalyst composition without component Z. The addition of component Z reduces the ratio of ethylene to acetic acid produced whilst retaining high overall selectivity to ethylene and acetic acid. Thus, by using the catalyst compositions of the present invention, it is possible to produce a product stream comprising ethylene and acetic acid in an approximately 1:1 ratio, which may be subsequently used, without the need for the further addition of ethylene and acetic acid, in the production of vinyl acetate. By "approximately 1:1", as used herein, is meant a product stream in which the ratio of acetic acid to ethylene is between 0.8:1 and 1.2:1, preferably between 0.9:1 and 1.1:1.

A second aspect of the present invention relates to a process for the preparation of a catalyst composition according to the first aspect of the present invention, comprising the steps of:
(a) forming a mixture comprising molybdenum, vanadium, niobium, a support material or a precursor thereof, component Z, and optionally tungsten in a solution;
(b) drying the mixture to form a dried solid material; and
(c) calcining the dried solid material to form the catalyst composition.

The mixture comprising molybdenum vanadium, niobium, a support material or a precursor thereof, component Z, and optionally tungsten in a solution formed in step (a) of the second aspect of the present invention may also comprise a further component, Y, as previously defined, where this is a component of the catalyst composition.

Suitably the mixture comprising molybdenum, vanadium, niobium, support material, or a precursor thereof, component Z, optionally tungsten and optionally component Y may be formed by mixing compounds and/or complexes of each of the metals with the support material or precursor thereof in a suitable solvent. The solvent is preferably water. Most preferably the mixture is a solution in water having a pH in the range from 1 to 12, preferably from 2 to 8, at a temperature of from 20° to 100° C.

Preferably, the molybdenum is introduced in to the mixture in the form of ammonium salts such as ammonium heptamolybdate, or organic acids of molybdenum, such as acetates and oxalates. Other compounds of molybdenum which may be used include, for example, molybdenum oxides, molybdic acid and/or molybdenum chlorides.

Preferably, the vanadium is introduced in to the mixture in the form of ammonium salts, such as ammonium metavanadate or ammonium decavanadate, or organic acids of vanadium, such as acetates and oxalates. Other compounds of vanadium which may be used include, for example, as vanadium oxides and sulphates.

Preferably, the niobium is introduced in to the mixture in the form of ammonium salts, such as ammonium niobium oxalate. Other compounds of niobium, such as niobium chlorides, may also be used, preferably complexed with an oxalate, a carboxylic acid or similar coordinating compound to improve solubility.

The support material may be introduced to the mixture of the metal components as a preformed support material, such as, for example, as silica. Supports comprising two or more different support materials, for example, a mixture of titania and silica, may be introduced as a mixture of pre-formed support materials, such as pre-formed titania and pre-formed silica support materials. Alternatively, at least one of the support materials is introduced in the form of a suitable precursor thereof, for example, the silica may be introduced in the form of a silica sol or a silica-titania support may be introduced in the form of a SiTi co-gel. Suitable SiTi co-gels include SiTi 4150 co-gel produced by Davicat (Grace-Davison).

Preferably, component Z is introduced in to the mixture in the form of an acetate, oxide, alkoxide or oxalate salt. Other compounds of component Z which may be used include, for example, halides and ammonium salts of Z. For example, preferred tin compounds include tin (II) oxalate and ammonium hexafluorostannate. Most preferably, tin, where used, is introduced into the mixture in the form of a SnO2 sol, stabilized with tetramethylammonium hydroxide.

Generally, in step (a) of the second aspect of the invention, the mixture of compounds containing the elements is prepared by dissolving sufficient quantities of soluble metal compounds and dispersing any insoluble compounds so as to provide a desired gram-atom ratio of the elements in the catalyst composition. The support material or precursor thereof may be introduced at any suitable stage during mixing, but is preferably introduced after the preparation of a mixture of the molybdenum, vanadium, niobium, component Z, optional tungsten and optional component Y.

The solvent is then removed from the mixture by drying, preferably by spray-drying, to form a dried solid material. This dried solid material is then calcined to form the catalyst composition. Calcination is preferably performed by heating to a temperature of from 200 to 550° C., suitably in air or oxygen, for a period of from 1 minute to 24 hours.

The support typically comprises at least about 20% and/or up to about 90% by weight of the total weight of the catalyst composition. Preferably the support comprises at least 40 wt % of the total weight of the catalyst composition and/or up to 60 wt % of the total weight of the catalyst composition.

In a third aspect of the present invention there is provided a process for the production of acetic acid and ethylene from a gaseous mixture comprising ethane, and optionally ethylene, which process comprises contacting the gaseous mixture with a molecular oxygen-containing gas at elevated temperature in the presence of a catalyst composition as hereinbefore described.

Ethane and the optional ethylene may each be used in substantially pure form or admixed with one or more of nitrogen, methane, carbon dioxide and water in the form of steam, which may be present in major amounts, for example greater than 5 volume percent or one or more of hydrogen, carbon monoxide, $C_3/C_4$ alkanes and alkenes, which may be present in minor amounts, for example less than 5 volume percent.

The molecular oxygen-containing gas may be air or a gas richer or poorer in molecular oxygen than air, for example oxygen. A suitable gas may be, for example, oxygen diluted with a suitable diluent, for example nitrogen.

It is preferred to feed, in addition to ethane, optional ethylene and the molecular oxygen-containing gas, water (steam) because this can improve the selectivity to acetic acid.

The elevated temperature may suitably be in the range from 200 to 500° C., preferably from 200 to 400° C.

The pressure may suitably be atmospheric or superatmospheric, for example in the range from 1 to 50 bar, preferably from 1 to 30 bar.

The process of the third aspect may be a fixed bed or a fluidised bed process, preferably a fluidised bed process.

Operating conditions and other information applicable to the performance of the invention may be found in the aforesaid prior art, for example U.S. Pat. No. 4,250,346.

Typically, using the catalyst compositions of the present invention, the combined selectivity to acetic acid and ethylene is at least 70 mol %, preferably at least 75 mol %, such as at least 80 mol %.

As used herein, selectivity refers to a percentage that reflects the amount of desired acetic acid product produced as compared to the total carbon in the products formed:—

% selectivity=100*Moles of acetic acid produced/$S$ wherein S=the molar acid-equivalent sum (carbon basis) of all carbon-containing products, excluding the alkane in the effluent.

In an integrated process for the production of vinyl acetate wherein the first step is the oxidation of ethane (optionally with ethylene), it is desired to produce acetic acid and ethylene from the ethane oxidation step at an approximate ratio of ethylene to acetic acid of 1:1 since this is the optimum ratio for subsequent reaction of acetic acid and ethylene with oxygen to produce vinyl acetate.

Hence, in a fourth aspect, the present invention provides an integrated process for the production of vinyl acetate from a gaseous mixture comprising ethane, and optionally ethylene, which process comprises:

(i) contacting, in a first reaction zone, a gaseous mixture comprising ethane, and optionally ethylene, with a molecular oxygen-containing gas at elevated temperature in the presence of a catalyst composition as hereinbefore described to produce a first product stream comprising acetic acid and ethylene, and (ii) contacting, in a second reaction zone, at least a portion of said ethylene and at least a portion of said acetic acid from said first product stream with a molecular oxygen-containing gas at elevated temperature in the presence of a catalyst suitable for the production of vinyl acetate, to produce a second product stream comprising vinyl acetate.

The second reaction zone for the production of vinyl acetate may be a fixed bed reactor but is preferably a fluidised bed reactor.

The oxygen feed to the second reaction zone may be any suitable oxygen-containing gas, and may suitably be air or a gas richer or poorer in molecular oxygen than air. Suitably, the gas may be oxygen diluted with a suitable diluent, for example, nitrogen, argon or carbon dioxide. Preferably essentially pure oxygen is used as the oxygen feed.

The first product stream preferably comprises acetic acid and ethylene in an approximately 1:1 ratio.

In one embodiment the first product stream may be fed directly to the second reaction zone. In this embodiment, the ethylene and acetic acid are co-fed to the second reaction zone.

Alternatively, the first product stream may be treated, e.g. by conventional separation, to produce an ethylene-containing stream and an acetic acid containing stream from said product stream, and said ethylene and acetic acid containing streams may be fed separately to the second reaction zone. In particular, the ethylene-containing stream may comprise ethylene in substantially pure form or may comprise ethylene as a mixture with one or more of nitrogen, methane, ethane, carbon dioxide and water in the form of steam or one or more of hydrogen, $C_3/C_4$ olefins or alkanes.

Where the second reaction zone is a fluidised bed reactor, the acetic acid may be introduced into the reactor in liquid form or in vapour form. Where the second reaction zone is a fixed bed reactor then the acetic acid is preferably introduced in to the reactor in vapour form.

The production of vinyl acetate in the second reaction zone, when carried out in a fluidised bed reactor, may suitably be operated at a temperature from 100 to 400° C., preferably 140 to 210° C. and a pressure of $10^5$ to $2 \times 10^6$ Pa gauge (1 to 20 barg), preferably $6 \times 10^5$ to $1.5 \times 10^6$ Pa gauge (6 to 15 barg), especially $7 \times 10^5$ to $1.2 \times 10^6$ Pa gauge (7 to 12 barg).

Catalysts known in the art for the production of vinyl acetate may be used in the second reaction zone. Thus, catalysts active for the production of vinyl acetate which may be used in a second reaction zone may comprise, for example, catalysts as described in GB 1 559 540; U.S. Pat. No. 5,185,308 and EP-A-0672453 the contents of which are hereby incorporated by reference.

GB 1 559 540 describes a catalyst active for the preparation of vinyl acetate by the reaction of ethylene, acetic acid and oxygen, the catalyst consisting essentially of: (1) a catalyst support having a particle diameter of from 3 to 7 mm and a pore volume of from 0.2 to 1.5 ml/g, a 10% by weight water suspension of the catalyst support having a pH from 3.0 to 9.0, (2) a palladium-gold alloy distributed in a surface layer of the catalyst support, the surface layer extending less than 0.5 mm from the surface of the support, the palladium in the alloy being present in an amount of from 1.5 to 5.0 grams per litre of catalyst, and the gold being present in an amount of from 0.5 to 2.25 grams per litre of catalyst, and (3) from 5 to 60 grams per litre of catalyst of alkali metal acetate.

U.S. Pat. No. 5,185,308 describes a shell impregnated catalyst active for the production of vinyl acetate from ethylene, acetic acid and an oxygen containing gas, the catalyst consisting essentially of: (1) a catalyst support having a particle diameter from about 3 to about 7 mm and a pore volume of 0.2 to 1.5 ml per gram, (2) palladium and gold distributed in the outermost 1.0 mm thick layer of the catalyst support particles, and (3) from about 3.5 to about 9.5% by weight of potassium acetate wherein the gold to palladium weight ratio in said catalyst is in the range 0.6 to 1.25.

EP-A-0672453 describes palladium containing catalysts and their preparation for fluidised bed vinyl acetate processes.

Preferably, the catalyst suitable for the production of vinyl acetate comprises a Group VIII metal, a catalyst promoter and an optional co-promoter. With regards to the Group VIII metal, the preferred metal is palladium. Suitable sources of palladium include palladium (II) chloride, sodium or potassium tetrachloropalladate, (II), ($Na_2PdCl_4$ or $K_2PdCl_4$), palladium acetate, palladium (II) nitrate or palladium (II) sulphate. The metal may be present in a concentration of greater than 0.2% by weight, preferably greater than 0.5% by weight based upon total weight of catalyst. The metal concentration may be as high as 10% by weight.

In addition to the Group VIII metal, the catalyst suitable for the production of vinyl acetate may comprise a promoter.

Suitable promoters include gold, copper, cerium or mixtures thereof. A preferred promoter is gold. Suitable sources of gold include gold chloride, tetrachloroauric acid (HAuCl$_4$), NaAuCl$_4$, KAuCl$_4$, dimethyl gold acetate, barium acetoaurate or gold acetate. The preferred gold compound is HAuCl$_4$. The promoter metal may be present in an amount of from 0.1 to 10% by weight in the finished catalyst.

The catalyst suitable for the production of vinyl acetate may also comprise a co-promoter material. Suitable co-promoters include Group I, Group II, lanthanide or transition metals, for example cadmium, barium, potassium, sodium, manganese, antimony, and/or lanthanum, which are present in the finished catalyst as salts, e.g. an acetate salt. The preferred salts are potassium or sodium acetate. The co-promoter is preferably present in the catalyst composition in a concentration of 0.1 to 15% by weight of catalyst, more preferably, from 1 to 5% by weight.

Where a liquid acetic acid feed is used the preferred concentration of co-promoter salt is up to 6% by weight, especially 2.5 to 5.5%. Where the acid is introduced in the vapour phase the co-promoter salt is preferably present in a concentration up to 11 wt %.

The catalyst suitable for the production of vinyl acetate may be a supported catalyst. Suitable catalyst supports include porous silica, alumina, silica/alumina, titania, silica/titania or zirconia. In particular for use in a fluidised bed process, the support is preferably silica, and, suitably, the support may have a pore volume from 0.2 to 3.5 mL per gram of support, a surface area of 5 to 800 m$^2$ per gram of support and an apparent bulk density of 0.3 to 1.5 g/mL.

The catalyst suitable for the production of vinyl acetate may be prepared by any suitable method. For example the catalyst for the production of vinyl acetate may be prepared by the method detailed in EP-A-0672453.

Advantageously, in the fourth aspect of the present invention, high concentrations of ethylene are fed to the second reaction zone. High concentrations of ethylene (greater than 50 mol % of the total feed) fed to the second reaction zone maximize the selectivity to vinyl acetate.

Desirably, the concentration of ethylene fed to the second reaction zone is at least 50 mol % of the total feed to the second reaction zone, preferably, at least 55 mol %, more preferably at least 60 mol %. Suitably, the concentration of ethylene is up to 85 mol % of the total feed to the second reaction zone, preferably, in the range at least 50 mol % to 80 mol %, such as at least 55 mol % to 80 mol %.

Production of vinyl acetate by reaction of ethylene, acetic acid and oxygen in which the combined feed to the vinyl acetate reaction comprises at least 60 mol % is described in EP 0985 657 A1, the contents of which are herein incorporated by reference.

A ratio of ethylene to acetic acid of approximately 1:1 is also the optimum ratio for an integrated process for the production of ethyl acetate.

Thus, the catalyst composition of the present invention may also be utilized in an integrated process for the production of ethyl acetate.

Hence, in a fifth, aspect, the present invention provides an integrated process for the production of ethyl acetate from a gaseous mixture comprising ethane, and optionally ethylene, which process comprises:

(i) contacting, in a first reaction zone, a gaseous mixture comprising ethane, and optionally ethylene, with a molecular oxygen-containing gas at elevated temperature in the presence of a catalyst composition as hereinbefore described to produce a first product stream comprising acetic acid and ethylene, and (ii) contacting, in a second reaction zone, at least a portion of said ethylene and at least a portion of said acetic acid from said first product stream, and optionally water, at elevated temperature in the presence of a catalyst suitable for the production of ethyl acetate, to produce a second product stream comprising ethyl acetate.

The second reaction zone for the production of ethyl acetate may be a fixed bed reactor but is preferably a fluidised bed reactor.

The first product stream preferably comprises acetic acid and ethylene in an approximately 1:1 ratio.

In one embodiment the first product stream may be fed directly to the second reaction zone. In this embodiment, the ethylene and acetic acid are co-fed to the second reaction zone.

Alternatively, the first product stream may be treated, e.g. by conventional separation, to produce an ethylene-containing stream and an acetic acid containing stream from said first product stream, and said ethylene and acetic acid containing streams may be fed separately to the second reaction zone. In particular, the ethylene-containing stream may comprise ethylene in substantially pure form or may comprise ethylene as a mixture with one or more of nitrogen, methane, ethane, carbon dioxide and water in the form of steam or one or more of hydrogen, C$_3$/C$_4$ olefins or alkanes.

Preferably, in the fifth aspect of the present invention, the concentration of ethylene fed to the second reaction zone is at least 50 mol % of the total feed to the second reaction zone, preferably, at least 55 mol %, more preferably at least 60 mol %.

Catalysts known in the art for the production of ethyl acetate may be used in the fifth aspect of the process of the present invention. Catalysts active for the production of ethyl acetate which may be used in the second reaction zone may comprise, for example, catalysts as described in EP-A-0926126, the contents of which are hereby incorporated by reference.

EP-A-0926126 describes a process for the production of esters by reacting, in a plurality of reactors set up in series, ethylene, propylene or mixtures thereof with a saturated aliphatic C$_1$-C$_4$ mono-carboxylic acid in the presence of a heteropolyacid catalyst.

The present invention will now be further illustrated by reference to the following Examples.

Catalyst Preparation

Comparative Catalyst A

Mo$_{1.00}$V$_{0.529}$Nb$_{0.124}$O$_x$ (=Mo$_{60.5}$V$_{32}$Nb$_{7.5}$O$_x$) on Silica The following three solutions were prepared:

Solution A: 214 g of ammonium heptamolybdate was dissolved in 250 g of water at 45° C. with stirring.

Solution B: 75 g of ammonium metavanadate was added to 725 g of water in a 2-liter beaker and heated to 80° C. The ammonium metavanadate did not completely dissolve.

Solution C: 74 g of ammonium niobium oxalate was added to 275 g of water in a 6-liter stainless steel beaker and heated to 45° C. A sol formed within 30 minutes.

Solution C was added to solution B and allowed to digest at 80° C. for 30 minutes. Solution A was then added to the mixture, which was then stirred for 15 minutes at medium heat.

638 grams of silica sol (Nalco 41D01) was then added to the stirred mixture.

The slurry was homogenized at 10,000 rpm for approximately 2 minutes. Spray drying was done in a mini-Niro spray-drier immediately after the solution was homogenized. Spray drying conditions were as follows: an inlet temperature of 290° C. inlet and an outlet temperature of 138° C.

The catalyst composition was calcined in air for 3 hours at 375° C. in a static muffle furnace before use.

The resulting spray-dried catalyst composition has a nominal composition $Mo_{60.5}V_{32}Nb_{7.5}O_x$ on silica, and at a nominal metal loading of 50% of the total catalyst weight.

Catalyst B

Catalyst B has a similar nominal composition as Comparative Catalyst A, but with the further addition of tin at a gram atom ratio of 0.33.

The catalyst composition was prepared as described for Catalyst A, but $SnO2$ sol, stabilized with tetramethylammonium hydroxide was used as the tin source.

Catalyst C

Catalyst C has a similar nominal composition as Catalyst B, except that approximately half of the tin was replaced by titanium, to give a catalyst with a nominal composition comprising tin and titanium each at a gram atom ratio of 0.165.

The catalyst composition was prepared as described for Catalyst A, but $SnO2$ sol, stabilized with tetramethylammonium hydroxide was used as the tin source and titanium isopropoxide was used as the titanium source.

Catalyst D

Catalyst D has a similar nominal composition as Catalyst B, but was supported on a silica-titania support.

The catalyst composition was prepared as described for Catalyst B, except that SiTi 4150, a co-gel supplied by Davison, was used as the support in place of the silica sol used in Catalyst B.

Catalyst E

Catalyst E has a similar nominal composition as Catalyst D, but was supported on a mixture of silica and silica-titania supports.

The catalyst composition was prepared as described for Catalyst B, except that SiTi 4150, a co-gel supplied by Davison and Nalco 41D01, silica sol, in a 50:50 ratio were used as support materials.

Comparative Catalyst F

Catalyst F has a similar nominal composition as Catalyst A, but with the further addition of Ti at a gram atom ratio of 0.33.

The catalyst composition was prepared as described for Catalyst A, but titanium isopropoxide was used as the titanium source.

Catalyst Testing

The catalyst compositions were tested in a fluidised bed reactor under the conditions indicated for each catalyst in the Tables below.

(HOS=Hours on stream, Sel=selectivity, STY=Space-Time Yield, Conv=conversion, Acetic=acetic acid, e/a=ethylene/acetic acid ratio)

The catalyst to be used for testing was sieved to obtain a specific particle size distribution (psd) of 70% 230/325 mesh (50/50), 25% pans (fines) and 5% greater than 170 mesh.

The catalyst (10 g) and an inert diluent with the same particle size distribution (St Gobain SA 539 alpha alumina, 43 g, density 1.27 g/ml) were added into a 40 cc fluidised bed reactor.

The reactions were typically performed at temperatures between 280° C. and 320° C. and at a reaction pressure of 16 barg. Ethane, ethylene (to mimic a recycle of ethylene), nitrogen and oxygen mixture was fed to the reactor using Brooks Mass Flow Controllers. Water was added by vaporisation and mixing with these feed gases prior to the reaction zone.

The volatile reactor effluent was sampled and analyzed by gas liquid chromatography whereas water and acetic acid were condensed and analyzed by gas liquid chromatography. The reactor bed temperature was monitored by a moving thermocouple.

Comparative Catalyst A

Run Conditions (Feed Mol %)

| HOS | Max T ° C. | Total Flow ml/min | GHSV $h^{-1}$ | $C_2H_6$ | $C_2H_4$ | $H_2O$ | $O_2$ | $N_2$ |
|---|---|---|---|---|---|---|---|---|
| 1-22 | 289 | 462 | 3200 | 60.0 | 5.0 | 5.0 | 6.5 | 23.5 |
| 24-48 | 302 | 462 | 3200 | 60.0 | 5.0 | 5.0 | 6.5 | 23.5 |
| 49-70 | 311 | 462 | 3200 | 60.0 | 5.0 | 5.0 | 6.5 | 23.5 |
| 71-92 | 317 | 462 | 3200 | 60.0 | 5.0 | 5.0 | 6.5 | 23.5 |

Results

| HOS Avg | Max T ° C. | Sel $C_2H_4$ % | Acetic % | $CO_x$ % | STY $C_2H_4$ | Acetic | $CO_x$ | Conv % $C_2H_6$ | $O_2$ | e/a |
|---|---|---|---|---|---|---|---|---|---|---|
| 1-22 | 289 | 62 | 29 | 10 | 54 | 53 | 21 | 5 | 48 | 2.2 |
| 24-48 | 302 | 61 | 30 | 10 | 77 | 81 | 30 | 7 | 68 | 2.1 |
| 49-70 | 311 | 60 | 30 | 10 | 98 | 105 | 40 | 8 | 85 | 2.0 |
| 71-92 | 317 | 60 | 29 | 10 | 107 | 111 | 4 | 9 | 93 | 2.1 |

These results show that the Comparative Catalyst A, which contains no component Z, produces ethylene and acetic acid with good overall selectivity, but at a high ratio of ethylene to acetic acid (e/a) of approximately 2:1.

Catalyst B

Run Conditions (Feed Mol %)

| HOS | Max T ° C. | Total Flow ml/min | GHSV $h^{-1}$ | $C_2H_6$ | $C_2H_4$ | $H_2O$ | $O_2$ | $N_2$ |
|---|---|---|---|---|---|---|---|---|
| 1-24 | 295 | 462 | 3200 | 60.0 | 5.0 | 5.0 | 6.5 | 23.5 |
| 25-47 | 309 | 462 | 3200 | 60.0 | 5.0 | 5.0 | 6.5 | 23.5 |
| 49-70 | 280 | 462 | 3200 | 60.0 | 5.0 | 5.0 | 6.5 | 23.5 |

Results

| HOS Avg | Max T °C. | Sel C$_2$H$_4$ % | Acetic % | CO$_x$ % | STY C$_2$H$_4$ | Acetic | CO$_x$ | Conv % C$_2$H$_6$ | O$_2$ | e/a |
|---|---|---|---|---|---|---|---|---|---|---|
| 1-24 | 295 | 40 | 42 | 18 | 37 | 83 | 39 | 6 | 76 | 1.0 |
| 25-47 | 309 | 42 | 40 | 18 | 49 | 102 | 52 | 7 | 95 | 1.0 |
| 49-70 | 280 | 41 | 43 | 16 | 27 | 60 | 24 | 4 | 49 | 1.0 |

These results show that the Catalyst B, which contains tin as component Z, produces ethylene and acetic acid with good overall selectivity and at a ratio of ethylene to acetic acid of approximately 1:1. Hence, addition of Sn to the catalyst composition has allowed the ratio of ethylene to acetic acid to be reduced, whilst maintaining high overall selectivity, compared to the Comparative Catalyst A.

Catalyst C

Run Conditions (Feed Mol %)

| HOS | Max T °C. | Total Flow ml/min | GHSV h$^{-1}$ | C$_2$H$_6$ | C$_2$H$_4$ | H$_2$O | O$_2$ | N$_2$ |
|---|---|---|---|---|---|---|---|---|
| 2-29 | 277 | 462 | 3200 | 60.0 | 5.0 | 5.0 | 6.5 | 23.5 |
| 30-51 | 296 | 462 | 3200 | 60.0 | 5.0 | 5.0 | 6.5 | 23.5 |
| 53-73 | 325 | 462 | 3200 | 60.0 | 5.0 | 5.0 | 6.5 | 23.5 |

Results

| HOS Avg | Max T °C. | Sel C$_2$H$_4$ % | Acetic % | CO$_x$ % | STY C$_2$H$_4$ | Acetic | CO$_x$ | Conv % C$_2$H$_6$ | O$_2$ | e/a |
|---|---|---|---|---|---|---|---|---|---|---|
| 2-29 | 277 | 42 | 42 | 16 | 21 | 45 | 18 | 3 | 34 | 1.0 |
| 30-51 | 296 | 43 | 39 | 19 | 36 | 70 | 35 | 5 | 57 | 1.1 |
| 53-73 | 325 | 40 | 39 | 21 | 50 | 102 | 63 | 7 | 93 | 1.0 |

These results show that the Catalyst C, which contains tin as component Z and titanium as a component Y, produces ethylene and acetic acid with good overall selectivity and at a ratio of ethylene to acetic acid of approximately 1:1. Hence, addition of Sn and Ti to the catalyst composition has allowed the ratio of ethylene to acetic acid to be reduced, whilst maintaining high overall selectivity, compared to the Comparative Catalyst A.

Catalyst D

Run Conditions (Feed Mol %)

| HOS | Max T °C. | Total Flow ml/min | GHSV h$^{-1}$ | C$_2$H$_6$ | C$_2$H$_4$ | H$_2$O | O$_2$ | N$_2$ |
|---|---|---|---|---|---|---|---|---|
| 15 | 285 | 432 | 3190 | 59.5 | 5.0 | 4.9 | 6.3 | 24.3 |
| 19-21 | 297 | 432 | 3190 | 59.5 | 5.0 | 4.9 | 6.3 | 24.3 |
| 25-37 | 315 | 432 | 3190 | 59.5 | 5.0 | 4.9 | 6.3 | 24.3 |

Results

| HOS Avg | Max T °C. | Sel C$_2$H$_4$ % | Acetic % | CO$_x$ % | STY C$_2$H$_4$ | Acetic | CO$_x$ | Conv % C$_2$H$_6$ | O$_2$ | e/a |
|---|---|---|---|---|---|---|---|---|---|---|
| 15 | 285 | 18 | 61 | 22 | 18 | 130 | 49 | 3 | 45 | 0.3 |
| 19-21 | 297 | 20 | 57 | 23 | 28 | 168 | 72 | 4 | 62 | 0.4 |
| 25-37 | 315 | 23 | 53 | 24 | 48 | 234 | 114 | 5 | 92 | 0.5 |

These results show that the Catalyst D, which contains tin as component Z and Ti as part of the support, produces ethylene and acetic acid with good overall selectivity but at a ratio of ethylene to acetic acid of less than 1:1. Hence, addition of Sn and Ti to the catalyst composition has allowed the ratio of ethylene to acetic acid to be reduced, whilst maintaining high overall selectivity, compared to the Comparative Catalyst A.

Catalyst E

Run Conditions (Feed Mol %)

| HOS | Max T °C. | Total Flow ml/min | GHSV $h^{-1}$ | $C_2H_6$ | $C_2H_4$ | $H_2O$ | $O_2$ | $N_2$ |
|---|---|---|---|---|---|---|---|---|
| 2-24 | 293 | 463 | 3190 | 60.0 | 5.1 | 4.9 | 6.7 | 23.3 |
| 25-45 | 315 | 463 | 3190 | 60.0 | 5.1 | 4.9 | 6.7 | 23.3 |

Results

| HOS Avg | Max T °C. | Sel $C_2H_4$ % | Acetic % | $CO_x$ % | STY $C_2H_4$ | Acetic | $CO_x$ | Conv % $C_2H_6$ | $O_2$ | e/a |
|---|---|---|---|---|---|---|---|---|---|---|
| 2-24 | 293 | 28 | 51 | 21 | 25 | 96 | 43 | 4 | 68 | 0.5 |
| 25-45 | 315 | 32 | 47 | 21 | 42 | 130 | 67 | 6 | 99 | 0.7 |

These results show that the Catalyst E, which contains tin as component Z and Ti as part of the support, produces ethylene and acetic acid with good overall selectivity but at a ratio of ethylene to acetic acid of less than 1:1. Hence, addition of Sn and Ti to the catalyst composition has allowed the ratio of ethylene to acetic acid to be reduced, whilst maintaining high overall selectivity, compared to the Comparative Catalyst A.

Catalyst F

Run Conditions (Feed Mol %)

| HOS | Max T °C. | Total Flow ml/min | GHSV $h^{-1}$ | $C_2H_6$ | $C_2H_4$ | $H_2O$ | $O_2$ | $N_2$ |
|---|---|---|---|---|---|---|---|---|
| 0-194 | 310-320 | 428 | 3200 | 60.2 | 5.0 | 5.0 | 6.5 | 23.3 |

Results

| HOS Avg | Max T °C. | Sel $C_2H_4$ % | Acetic % | $CO_x$ % | STY $C_2H_4$ | Acetic | $CO_x$ | Conv % $C_2H_6$ | $O_2$ | e/a |
|---|---|---|---|---|---|---|---|---|---|---|
| 176-194 | 320 | 6 | 60 | 33 | 8 | 165 | 100 | 5 | 100 | 0.1 |

These results show that the Comparative Catalyst F, which contains titanium as a catalyst component but does not comprise a Group 14 metal produces predominantly acetic acid.

Comparison of Catalysts B, D and E shows that the addition of Ti as part of the support also influences the ratio of ethylene to acetic acid produced.

Comparison of Catalysts C, D and E with F shows that the addition of Sn and Ti mitigates the effect of Ti alone, allowing the ratio of ethylene to acetic acid to be tailored to approximately 1:1.

The invention claimed is:

1. A process for the production of acetic acid and ethylene from a gaseous mixture comprising ethane and optionally ethylene, which process comprises contacting in a reaction zone the gaseous mixture with a molecular oxygen containing gas at elevated temperature in the presence of a catalyst composition, which catalyst composition consists of the elements molybdenum, vanadium and niobium, optionally tungsten and a component Z and optionally component Y, in combination with oxygen, wherein a, b, c, d, e and f represent the gram atom ratios of the elements Mo, W, Z, V, Nb and Y respectively, such that:

$0 < a \leq 1; 0 \leq b < 1$ and $a+b=1$;

$0.05 < c \leq 2$;

$0 < d \leq 2$;

$0 < e \leq 1$; and $0 \leq f \leq 2$;

wherein Z is selected from the group consisting of Ge, Sn and Pb, and Y is selected from the group consisting of Cr, Mn, Ta, B, Al, Ga, In, Pt, Zn, Cd, Bi, Ce, Co, Rh, Ir, Cu, Ag, Fe, Ru, Os, K, Rb, Cs, Mg, Ca, Sr, Ba, Ni, P, Si, Tl, U, Re, La, Ti, Hf and Zr, said elements being supported on a support, and wherein acetic acid and ethylene are produced in a ratio in the range of 0.8:1 to 1.2:1.

2. A process according to claim 1 wherein $0.01 < a \leq 1$, $0.1 \leq c \leq 2$, $0.1 \leq d \leq 2$, $0.01 < e \leq 1$.

3. A process according to claim 2 wherein $0.1 \leq d \leq 0.5$.

4. A process according to claim 2 wherein $0.01 \leq e \leq 0.6$.

5. A process according to claim 1 wherein Z is Sn.

6. A process according to claim 1 wherein Y is selected from the group consisting of Bi, Ca, Ce, Cu, K, P, La, Hf, Zr, and Ti.

7. A process according to claim 6 wherein Y is selected from the group consisting of Hf, Ti, and Zr.

8. A process according to claim 7 wherein Y is Ti.

9. A catalyst composition process according to claim 1 wherein the catalyst composition comprises Sn and further comprises, as component Y, Ti.

10. A process according to claim 9 wherein $0.01 \leq f \leq 0.5$.

11. A process according to claim 1 wherein the support comprises at least one metal oxide support.

12. A process according to claim 1 wherein the support is selected from the group consisting of silica, titania, titanosilicates, alumina, aluminosilicates, zirconia and mixtures thereof.

13. A process according to claim 12 wherein the support is selected from the group consisting of silica, titania and a mixture of silica and titania.

14. A process according to claim 1 wherein the support is a non-oxide support.

15. A process according to claim 1 in which the support comprises from about 20 wt % to 90 wt % of the total weight of the catalyst composition.

16. A process according to claim 15 wherein the support comprises from 40 wt % to 60 wt % of the total weight of the catalyst composition.

17. A process according to claim 1 in which at least one of aluminium, titanium and zirconium is present in the composition as a component of the support and/or as component Y.

18. A process according to claim 1 wherein the gaseous mixture comprises ethane and ethylene.

19. A process according to claim 1 in which water is also present as a feed component.

20. A process according to claim 1 wherein the ratio of acetic acid to ethylene is in the range 0.9:1 to 1.1:1.

21. A process according to claim 1 wherein the elevated temperature is in the range 200 to 500° C.

22. A process according to claim 1 wherein the process is carried out at a pressure in the range of 1 to 50 bar.

23. A process according to claim 1 wherein the catalyst is used in the form of a fixed bed or a fluidised bed.

24. A process according to claim 1 wherein the overall selectivity to acetic acid and ethylene is at least 70 mol %.

25. A process according to claim 24 wherein the overall selectivity is at least 75 mol %.

26. A process as claimed in claim 1 in which at least a portion of the acetic acid and at least a portion of the ethylene is contacted in a second reaction zone with a molecular oxygen-containing gas at elevated temperature in the presence of a catalyst suitable for the production of vinyl acetate to produce vinyl acetate.

27. A process according to claim 26 wherein the second reaction zone is a fluidised bed reactor.

28. A process as claimed in claim 1 in which at least a portion of the acetic acid and at least a portion of the ethylene are contacted in a second reaction zone at elevated temperature in the presence of a catalyst suitable for the production of ethyl acetate to produce ethyl acetate.

* * * * *